United States Patent [19]

Dziobkowski et al.

[11] 3,997,657

[45] Dec. 14, 1976

[54] DRY SLIDE REAGENT EMPLOYED IN IMMUNOFLUORESCENT TEST FOR DETECTION OF HUMAN ANTINUCLEAR FACTOR

[75] Inventors: Beatrice Frances Dziobkowski, Burlington, Vt.; Gerald Earl Stiles, W. Nyack, N.Y.

[73] Assignee: American Cyanamid Company, Stamford, Conn.

[22] Filed: Dec. 3, 1975

[21] Appl. No.: 637,270

Related U.S. Application Data

[62] Division of Ser. No. 406,439, Oct. 15, 1973, abandoned.

[52] U.S. Cl. .................... 424/3; 23/253 TP; 424/8; 424/12; 424/85; 424/88; 427/2; 427/4
[51] Int. Cl.² ................. G01N 1/00; G01N 21/52; G01N 31/22
[58] Field of Search .............. 424/3, 7, 8, 12; 195/1.7, 1.8; 427/2, 4, 8; 23/253 TP

[56] References Cited

OTHER PUBLICATIONS

Dubois, JAMA, vol. 225, Aug. 6, 1973, p. 637.
Burrows, J. Med. Soc., NJ, vol. 68, 1971, pp. 647–649.
Miescher, J. of Immuno., vol. 85, 1960, pp. 27–36.
Friou, J. Immunol., vol. 80, 1958, pp. 324–329.
Iwasaki, Surg. Gyn & Obs., vol. 124, Jan. 1967, pp. 1–24.
Widelock, Am. J. Pub. Health, vol. 51, 1961, pp. 829–835.
Mellors, Anal. Cytology, 2nd ed. 1959, McGraw-Hill, N.Y. pp. 1–28, 438–441.

Primary Examiner—Albert T. Meyers
Assistant Examiner—A. P. Fogelson
Attorney, Agent, or Firm—C. F. Costello, Jr.; J. W. Richards

[57] ABSTRACT

A dry diagnostic reagent composed of specially prepared, fixed and stabilized fetal calf thymocytes on microscope slides ready for use in an immunofluorescent test for the detection of human anti-nuclear factor in human serum or plasma in the diagnosis of systemic lupus erythematosus and other autoimmune diseases.

4 Claims, No Drawings

DRY SLIDE REAGENT EMPLOYED IN IMMUNOFLUORESCENT TEST FOR DETECTION OF HUMAN ANTINUCLEAR FACTOR

This is a division of application Ser. No. 406,439 filed Oct. 15, 1973 now abandoned.

BACKGROUND OF THE INVENTION

This invention is concerned with a dry diagnostic reagent of improved sensitivity and susceptibility to quantification for use in the fluorescent method for the detection of antinuclear factor (ANF) in the diagnosis of systemic lupus erythematosus (SLE) and other autoimmune diseases composed of specially prepared, fixed and stabilized fetal calf thymocytes.

The fluorescent antibody technique for the detection of antinuclear factor in the diagnosis of systemic lupus erythematosus and other autoimmune diseases using nuclear cell material, including calf thymus nuclei, is known. Friou, G. J., et al., Journal of Immunology, Vol 80, 324–329 (1958); Widelock, D., et al., Am. J. Pub. Health, 51, 829–835 (1961); Keffer, J. H., Proc. Ann. Meeting, College Am. Path. and Ann. Soc. Clin. Path., No. 16, pg. 87 (1970); and Burrows, S, et al., Jour. Med. Soc. N.J., Vol. 68, pgs. 647–649 (1971).

Friou et al., supra, have demonstrated that the fluorescent antibody technic can be utilized to illustrate the union of lupus erythematosus (LE) serum factor with nuclear material. Of special interest is Friou et al's., demonstration of the usefulness of the fluorescent antibody technic in the diagnosis of SLE. Friou et al., reported that calf thymus nuclei were satisfactory for the detection of the SLE factor and concluded that the most satisfactory preparation for testing human sera for SLE factor was calf thymus nuclei.

In Friou et al., a drop of a dilute suspension of calf thymus nuclei was allowed to dry on a gelatin-coated slide. The slide was then flooded with the serum being tested and allowed to stand in a moist tray for 30 minutes. It was then washed with isotonic buffered saline, pH 7.0, for 10 minutes. Finally the material was exposed to slightly diluted fluorescent conjugate for 30 minutes, washed again, mounted in buffered glycerol under a cover slip and examined.

Widelock et al., supra, also report on work with a fluorescent antibody procedure for lupus erythematosus using calf thymus cells. Widelock et al. conclude that screening for systemic lupus erythematosus using the fluorescent antibody technique with calf thymus nuclei was more sensitive than the performance of other tests and that diseases other than SLE were found to be positive by such technique. Widelock et al. report that the use of calf thymus nuclei necessitated obtaining a fresh calf thymus gland which should be frozen at −40° C. within four hours after death of the animal and that decreasing sensitivity of the test was observed as the calf thymus aged. The fluorescent technic of Widelock et al., utilizing calf thymus cells, was based on the method described by Friou et al., supra. The Widelock et al. report is essentially a confirmation of the previous report by Friou et al., supra.

In Proc. Annual Meeting, College of Am. Path. and Ann. Soc. Clin. Path., Sept. 11–19, 1970, page 87, Keffer, J. H., notes the value of fluorescent antinuclear antibody testing as an objective replacement for the "L.E. Cell Test" and emphasizes the simplicity of fluorescent microscopy. Although not so reported in the aforementioned Keffer, J. H. publication, Keffer, J. H. has used fetal calf thymus as a source of thymocytes in fluorescent antinuclear antibody testing. However, Keffer, J. H.'s known work did not involve a dry diagnostic reagent composed of specially prepared, fixed and stabilized fetal calf thymocytes on a microscope slide ready for use in an immunofluorescent test for the detection of human antinuclear factor in human serum or plasma as set forth herein.

Barnes, R., et al., in Ann. rheum. Dis. 21:287–291 (1962) report on a comparison between a commercial preparation of nucleoprotein coated latex particles and the fluorescent method for the detection of serum antinuclear factor and conclude that the nucleoprotein coated latex particle does not appear to be a satisfactory substitute for the immunofluorescent technique. Barnes, R., et al., appear to have used human or bovine thyroid as a source of thymocytes.

The combination of features which distinguish the present invention from the above publications include: the use of fetal calf thymus as a source of thymoctyes; sieving to isolate individual cells; preparing smears of thymocytes on microscope slides by air-drying and chemical fixation; and fixed and stabilized thymocyte slides ready for use in an air-tight container with dessicant. The diagnostic reagent of the present invention is fixed (dried chemically) on the slide ready for instant use in the detection of antinuclear factor and the diagnosis of SLE and other autoimmune diseases. The reference products require slide preparation.

The diagnostic reagent of the present invention can be utilized by hospitals, clinical laboratories and by physicians as a diagnostic reagent for use in the fluorescent antinuclear factor test for the detection and quantitation of serum factors associated with autoimmune diseases such as systemic lupus erythematosus (SLE). Other "autoimmune diseases" which may be diagnosed by this reagent include connective tissue diseases, rheumatoid arthritis, szleroderma and dermatomyositis. The invention disclosed herein provides a reagent for the lupus erythematosus fluorescent ANF test that is convenient, ready to use, stable, highly sensitive and lends itself to standardization.

SUMMARY OF THE INVENTION

Briefly, the invention is concerned with a dry diagnostic reagent composed of specially prepared, fixed and stabilized fetal calf thymocytes for use in the detection of antinuclear factor in human serum in the diagnosis of systemic lupus erythematosus and other related autoimmune diseases, its method of preparation, a method of using it in immunofluorescent tests for the detection of antinuclear factor in human serum in the diagnosis of systemic lupus erythematosus and other autoimmune diseases, and with a dianostic kit or pack containing said reagent for said use.

The invention contemplates a method for preparing a dry diagnostic reagent fixed on a microscope slide for the detection of human antinuclear factor in human serum or plasma in an immunofluorescent test for the diagnosis of systemic lupus erythematosus and other autoimmune diseases which comprises: sieving only fetal calf thymus to obtain dispersed thymocyte cells therefrom; suspending said dispersed thymocyte cells in isotonic buffered saline solution to a cell count of about $1.0$–$1.5 \times 10^6$ cells/ml.; placing at least one portion of about 0.05 ml. of said dispersed thymocyte cell suspension on a microscopic slide; drying said amount of said dispersed thymocyte cell suspension on said slide; fixing said dried cell suspension with modified Carnoy's solution; washing said fixed suspension with water; and drying said fixed and washed suspension.

The invention also contemplates a dry diagnostic reagent fixed on a microscope slide for the detection of human antinuclear factor in human serum or plasma in an immunofluorescent test for the diagnosis of systemic lupus erythematosus and other autoimmune diseases comprising the dry diagnostic reagent prepared by the method set forth herein.

The invention further contemplates the improvement in the detection of human antinuclear factor in human serum or plasma in immunofluorescent tests for the diagnosis of systemic lupus erythematosus and other autoimmune diseases which involves employing the dry diagnostic reagent prepared as set forth herein.

The invention also contemplates a diagnostic kit for use in the detection of human antinuclear factor in human serum or plasma in an immunofluorescent test for the diagnosis of systemic lupus erythematosus and other autoimmune diseases chiefly comprising fifteen microscope slides containing on each slide three stabilized smears of fetal calf thymocytes, prepared by the method set forth herein; a vial of positive systemic lupus erythematosus control serum obtained from SLE donors; a vial of negative systemic lupus erythematosus control serum obtained from non-SLE donors; and a vial of lyophilized rabbit antihuman globulin, fluorescein conjugated. The conjugate consists of rabbit antibody directed against human gamma globulin. The rabbit antibody is isolated from serum of rabbits hyperimmunized with human gamma globulin. The purified rabbit antibody is mixed with fluorescein isothiocyanate, re-purified and lyophilized. Information on the preparation of fluorescein conjugated antibody reagents can be found in G. A. Hebert et al., The Preparation and Physicochemical Characterization of Fluorescent Antibody Reagents (1972), U.S. Department of Health, Education and Welfare, Center for Disease Control, Atlanta, Ga.

The invention is further concerned with a method for the detection of human antinuclear factor in human serum using an immunofluorescent test for the diagnosis of systemic lupus erythematosus and other autoimmune diseases which comprises placing about 0.03 ml. of diluted human serum on about 0.05 ml. of a dried fetal calf thymocyte smear on a microscope slide prepared as set forth herein; placing about 0.03 ml. each of positive and negative systemic lupus erythematosus control sera on a second and third amount of 0.05 ml. of dried fetal calf thymocyte smears on said slide; incubating said slide; rinsing said incubated slide; washing said rinsed slide; adding about 0.03 ml. of diluted rabbit antihuman globulin fluorescein conjugate to each smear; spreading said conjugate uniformly to cover entire smear; repeating the incubating, rinsing, washing, adding and spreading steps noted above; mounting said slides; and examining said slides under fluorescent microscope using 100X magnification (lower power objective) and 440X magnification (high-dry objective).

The diagnostic reagent of this invention is made up only of fetal calf thymocytes. No other thymocytes are used or contemplated. Thymocytes are lymphoblast cells from thymus glands containing very large nuclei. As a calf grows the thymus becomes smaller. Therefore, thymi taken from calf fetuses are in their largest growth stage and hence, richer in thymocytes containing DNP.

In the practice of the invention, fetal calf thymi from 5 to 6 month calf fetus are collected and stored in physiological saline at 4° C. until use. The fetal calf thymocytes are obtained from the fresh fetal calf thymus with sieving. Sieving is a most important part of the present invention. It isolates the individual thymocyte cells and disperses them for standardization of smear cell count. Dispersal of thymocyte cells eliminates clumping and enhances visualization and interpretation of the test. In the sieving step the fetal thymi are squeezed through a wire sieve of an amnion squeezer or the like. In this way the cells are isolated and dispersed in a very efficient and practical manner. The dispersed cells are then suspended in an isotonic buffered saline solution to a cell count of about $1.0-1.5 \times 10^6$ cells/ml. Such suspension prevents rupture of the thymocyte cells. A cell count is made because there must be enough cells to be easily located under a microscope but not so many cells that they clump together in masses. One drop (about 0.05 ml.) of the counted cell suspension is then placed on one or more circles on a microscope slide, usually three circles to a slide, and dried. The cell suspension may be dried on the slide at room temperature or alternatively at about 37° C. with low humidity. The thymocycle slide is then fixed or stabilized in modified Carnoy's solution (75% absolute methanol: 25% glacial acetic acid), washed with water, air dried and stored in an air-tight container with dessicant, or frozen at −20° C. or below, ready for use in a fluorescent antinuclear factor test.

The microscope slide is fixed with modified Carnoy's solution to prevent decomposition of the thymocyte cells. The modified Carnoy's solution acts as a preservative and stabilizer which prevents breakdown of the cells and prevents the cells from being washed from the slide. Without Carnoy's solution there is no stability. Other fixing solutions cause either non-specific fluorescence, loss of cell integrity or loss of specific fluorescence. The slide is washed in distilled water and dried in air at room temperature to remove excess Carnoy's solution. After drying, the slides are put in an air tight container with a dessicant to prevent degradation of the thymocytes.

To perform the fluorescent antinuclear factor test using the diagnostic reagent of this invention, patient serum is incubated with the thymocyte smears on the slide so that antibodies to DNP, if present, can react with the DNP in the thymus nuclei and become bound. Unbound serum components are then washed off by several rinsings. The reaction is then visualized by adding animal antibody to human gamma globulin which has been conjugated with a fluorescence-emitting molecule such as fluorescein isothiocyanate. After an additional washing to remove non-specific fluoroescence the slide is examined under a microscope equipped with illumination and filters to express fluorescence; if the serum is positive, DNP antibody:DNP:antihuman globulin complex will be seen in the thymus nuclei.

DETAILED DESCRIPTION OF THE INVENTION

The invention will be more fully illustrated by reference to the following detailed description.

EXAMPLE 1

Procedure for Preparation of 2,000 Slides Containing Diagnostic Reagent Ready for Use A. Materials Modified Carnoy's solution.

| Absolute methanol | 75% |
|---|---|
| Glacial acetic acid | 25% |

Phosphate buffered saline (PBS), 0.05M, pH 7.1 ± 0.1.

| $NaH_2PO_4-H_2O$ | 1.93 g. | |
|---|---|---|
| $Na_2HPO_4$ | 5.11 g. | Q.S. $H_2O$ to 1 liter |
| NaCl | 5.70 g. | |

Reich slides (Bellco Glass).
Staining racks and dishes.
Drying equipment.
Amnion squeezer.
Fetal thymus (from a 5–6 month fetus) collected and delivered in physiological saline at 4° C.

B. Preparation of Fetal Calf Thymocyte Suspension
1. Remove a 10 g. portion of the fetal thymus and rinse in PBS.
2. Squeeze the 10 g. through amnion squeezer into a 500 ml. flask containing 250 ml. PBS. Rinse the squeezer with 250 ml. PBS bringing the final volume to 500 ml.
3. Pass the 500 ml. suspension through six (6) layers of gauze, then centrifuge at 170 × g. (IEC-PR6, Head No. 259, 800 r.p.m.) for 7–8 minutes in four 250 ml. centrifuge bottles.
4. Carefully remove supernate and pass it through a $c$ pore sintered glass filter.
5. Do a trypan blue cell count and adjust suspension to $1 \times 10^6$ cells/ml.

C. Preparation of Fetal Calf Thymocyte Slides
1. Place one drop (approximately 0.05 ml.) of the diluted cell suspension in the center of each ceramic ring on the Reich slides.
2. Dry suspension on slide with the aid of warm air.
3. When the smear is dry, place slide on edge in the staining rack — do not place slides back-to-back.
4. Immerse rack in fresh modified Carnoy's solution for ten minutes.
5. Rinse slides in PBS and wash by immersing in PBS for ten minutes. Use a separate bath for the rinse and wash.
6. Rinse salt off by dipping slides in three consecutive baths of distilled water.
7. Drain and dry slides.
8. Pack immediately, one dessicant package and 15 slides per container.

EXAMPLE 2

Test Procedure for Prepared Slides Containing Diagnostic Reagent

A. Materials p1 Phosphate Buffered Saline (PBS), pH 7.2 ± 0.1. Formula per liter:

| NaCl | 7.65 g. |
|---|---|
| $Na_2HPO_4$ | 0.724 g. |
| $KH_2PO_4$ | 0.21 g. |

Several liters may be prepared and stored at room temperature. Determine the pH of each lot of PBS. If the pH is above or below the 7.2 ± 0.1 value, adjust with normal NaOH or HCl.

Mounting Medium:
One part PBS, pH 7.2, plus 9 parts glycerine (reagent quality).

Microscopes adapted for fluorescent microscopy. An ultraviolet source such as an HBO 200W high pressure mercury lamp in combination with a BG12 exciting filter and a OG1 barrier filter will be satisfactory for routine use.

B. Procedure
1. Blood samples should be collected aseptically, avoiding hemolysis, and allowed to clot. Serum should be removed and refrigerated or frozen if not tested immediately. Do not heat inactive sera or controls.
2. Reconstitute lyophilized antihuman globulin with 1 ml. of distilled water.
3. Dilute the reconstituted antihuman globulin with phosphate buffered saline (PBS). The optimal concentration for each lot of conjugate has been predetermined. Since conditions and equipment vary from one laboratory to another, it may be desirable to determine dilution factor for each lot of antihuman globulin by testing with standard control sera. The solution selected is optimum when maximum fluorescence is obtained with the positive control serum and minimum fluorescence with the negative control serum.
4. Prepare a 1:10 dilution of the patient's serum in PBS.
    Note: Positive and negative controls should be run concurrently with each test. *Do not dilute control sera.*
5. Add approximately 0.03 ml. of diluted patient's serum to the first circle of the thymocyte microscope slide. Similarly add 0.03 ml. of positive and negative lupus AN-F control sera to the second and third circles. Take care not to overfill or allow mixing of sera.
6. Incubate slide for 30 minutes at room temperature in a moist atmosphere to prevent evaporation.
7. Rinse slides in PBS by placing slides in staining dish containing PBS for five minutes. Agitate slides by dipping them in and out of the PBS.
8. Using fresh PBS, repeat washing procedure.
9. Remove slides from water, shake excess fluid from slides and blot periphery with bibilous paper.
10. Add approximately 0.03 ml. of diluted conjugate to each circle-smear. Spread uniformly with an applicator to cover entire smear.
11. Repeat steps 6, 7, 8, 9 and 10.
12. Mount slides immediately by placing a small drop of mounting medium on each smear and apply a 24 × 50 mm. cover glass.
13. Examine slides as soon as possible. If a delay in reading is necessary, place slides in the dark at 4° C. and read within four hours.
14. Examine smears with fluorescent microscope using 100X magnification (low power objective) and 450X magnification (high-dry objective).

EXAMPLE 3

Test Procedure for Prepared Slides Containing Diagnostic Reagent Using Diagnostic Kit As set forth herein, this invention is also concerned with a diagnostic kit[1] for the detection of human antinuclear factor comprising fetal calf thymocyte slides prepared according to this invention. Such diagnostic kit chiefly comprises glass slides containing fetal calf thymocytes thereon, a vial containing antihuman globulin, fluorescein conjugated (lyophilized rabbit antihuman globulin conjugated with fluorescein isothiocyanate), a vial containing positive lupus AN-F human reference serum and a vial containing negative lupus AN-F human reference serum.

[1] Lederle Diagnostic Fluorescent Antinuclear Factor (AN-F) Test Kit, Lederle Diagnostics American Cyanamid Company, Pearl River, N.Y.

The invention is illustrated in kit form as follows

The Fluorescent Antinuclear Factor (AN-F) Test Kit is to be used for the immunofluorescent test for the detection of human antinuclear factors associated with systemic lupus erythematosus. The test is packaged as a multiple test kit, each kit sufficient for 45 determinations.

The AN-F test is based upon the principle of the fluorescent antibody technique, publications, supra. The specific antibody antigen reaction involved is the binding of serum antinuclear factors to nuclear components of fetal calf thymocytes. The use of calf thymocytes as a substrate for the detection of antinuclear factors has been cited, supra.

Smears of fetal calf thymocytes have been specifically prepared to be the substrate for the Fluorescent AN-F Test. Using the reagents and materials provided, the Fluorescent AN-F Test is easily performed, especially when compared with the standard LE Cell Test. Relatively inexpensive equipment can be used successfully with widely available standard microscopes.

Materials Supplied in Kit
- 15 3-ringed microscope slides with stabilized smears of fetal calf thymocytes.
- 1 Squeeze Vial-1 ml. AN-F Positive Control Serum (Human).
- 1 Squeeze Vial-1 ml. AN-F Negative Control Serum (Human).
- 1 Vial-1 ml. Rabbit Antihuman Globulin, Fluorescein Conjugated, Lyophilized.

Laboratory Equipment and Materials Needed Not Supplied in Kit
1. Fluorescence microscope.
2. Cover glasses (24 × 50 mm).
3. Staining dishes and racks.
4. Bibulous paper.
5. Pasteur pipettes (approximately 0.03 ml. delivery).
6. Serologic test tubes.
7. Phosphate buffered saline (PBS). See formula.
8. Glycerol (reagent grade). See formula for mounting media.

Fluorescent Microscopy

Most microscopes can be adapted for fluorosecent microscopy. Any one of the following lamp, filter and condenser combinations has been recommended for AN-F testing.

Lamp and Filter Combinations for Fluorescent AN-F Test.
1. HBO 200 Lamp
   BG-22 Heat filter
   BG-12 (702) Exciter filter (3–4 mm. thickness)
   OG-1 (724) Barrier filter (orange)
   Dark field condenser
2. HBO 200 Lamp
   BG-22 Heat filter
   BG-38 Exciter filter
   BG-12 (702) Exciter filter (3–4 mm. thickness)
   OG-1 (724) Barrier filter (orange)
   Bright field condenser
3. HBO 200 Lamp
   BG-22 Heat filter
   UG-1 Exciter filter (2 or 4 mm. thickness)
   OG-1 (724) Barrier filter (orange)
   Dark field condenser
4. HBO 200 Lamp
   BG-22 Heat filter
   BG-38 Exciter filter
   OG-1 (724) Barrier filter (orange)
   UG-1 Exciter filter (2 or 4 mm. thickness)
   Bright field condenser
5. HBO 200 Lamp
   BG-22 Heat filter
   BG-12 (702) Exciter filter (3–4 mm. thickness)
   Corning 5840 (693) Exciter filter (2 mm. thickness)
   GG-9 (723) Barrier filter
   Dark field or bright field condenser
6. Quartz iodide lamp
   BG-12 (702) Exciter filter
   Corning 5113 (695) Exciter filter
   Barrier filter
   Bright field condenser
7. Tungsten filament lamp 6 or 12 V at maximum Voltage (rheostat) setting
   BG-12 (702) Exciter filter (4 mm. thickness)
   OG-1 (724) Barrier filter or Kodak filter No. 15 or 16, gelatin sheet placed prior to the eyepiece.
   Bright field condenser.

Directions For Use of Kit

Sample:
1. Blood samples should be collected aseptically, avoiding hemolysis, and allowed to clot. Serum should be removed and refrigerated or frozen if not tested immediately.
2. Do not heat inactive sera or controls.

Procedure:
1. Reconstitute lyophilized antihuman globulin with 1 ml. of distilled water.
2. Dilute the reconstituted antihuman globulin with phosphate buffered saline (PBS).

| NaCl | 5.7 Grams |
| Na$_2$HPO$_4$ | 5.11 Grams |
| NaH$_2$PO$_4$H$_2$O | 1.93 Grams |
| Distilled Water | 1000 ml. |

Several liters may be prepared and stored at 4° C. Determine the pH of each lot of PBS. If the pH is above or below the 7.1 ± 0.1 value, adjust with normal NaOH or HCl. The optimal concentration for each lot of conjugate has been predetermined and is noted on the label. Dispense the diluted conjugate in small amounts and store frozen. Since conditions and equipment vary from one laboratory to another, it may be desirable to determine the optimum working dilution for each lot of antihuman globulin. This is accomplished by testing serial dilutions of the antihuman globulin in PBS against the AN-F positive and negative control sera. The optimal working dilution is the dilution that gives maximum fluorescence with the postive control and minimum fluorescence with the negative control serum. Reconstituted and diluted conjugate should not be left at room temperature or exposed to light for extended periods. Avoid repeated freezing and thawing.

3. Prepare a 1:10 dilution of the patient's serum in PBS, Note: Positive and negative controls should be run concurrently with each test. Do not dilute control sera.
4. Add one drop (approximately 0.03 ml.) of diluted patient's serum to the first circle of the AN-F microscope slide. Similarly add one drop of positive and negative AN-F control sera to the second and third circles. Care should be taken not to overfill or allow mixing of sera. If necessary, a deeper well can be created by marking the periphery of each circle with a soft wax crayon.
5. Incubate slides for 30 minutes at room temperature in a moist atmosphere to prevent evaporation.
6. Rinse slides in PBS by placing them in a staining dish containing PBS for five minutes. Agitate slides by dipping them in and out of the PBS.
7. Using fresh PBS, repeat rinse procedure twice (total rinse=15 minutes).
8. Remove slides from buffer, shake excess fluid from slides, and blot periphery with bibulous paper.
9. Add one drop (approximately 0.03 ml.) of diluted conjugate to each circle; smear and spread uniformly with an applicator to cover the entire smear.
10. Repeat steps 5, 6, 7 and 8.
11. Mount slides immediately by placing a small drop of mounting medium on each smear and apply a 24 × 50, mm. cover glass.

Mounting Medium

One part PBS, pH 7.1, plus 9 parts glycerol (reagent quality).

12. Examine slides as soon as possible. If a delay in reading is necessary, place slides in the dark at 4° C. and read within four hours.
13. Examine smears with fluorescent microscope using 100X magnification (low-power objective) and 440X magnification (high-dry objective).

Interpretation:
1. Positive LE sera may show several patterns of fluorescence. Homogeneous or diffuse nuclear staining and peripheral or shaggy nuclear staining are the most common. The latter is generally seen only in strongly reactive sera.
2. The degree of fluorescence is estimated by eye and the brightness, when compared with the negative and positive controls, is recorded on some simple scale such as that listed below.
   −  Negative (including ± and trace)
   +  Just visible fluorescence
   ++ Definite fluorescence
   +++ Bright fluorescence
3. Patients with rheumatoid arthritis, scleroderma dermatomyositis, and a variety of connective tissue disease states may be AN-F positive usually in low titers and low frequency. Initial testing at a 1:10 dilution will avoid a large number of nonspecific reactions and will provide a meaningfull level of test sensitivity and specificity.
4. It is recommended that patients with positive AN-F test at the 1:10 level should be retested and titered. Strongly positive reactions with AN-F titers greater than 1:80-1:1:160 are often observed in patients with clinically indentifiable SLE. High AN-F titers are, therefore, strongly suggestive of SLE and can correlate with the activity of the disease.

Note: A strongly positive AN-F test does not confirm the diagnosis of SLE. Additional clinical and laboratory results are required for the prognosis and management of SLE patients.

5. A negative AN-F test at the 1:10 serum level virtually excludes a diagnosis of SLE since the fluorescent AN-F test is positive in over 99% of patients with SLE. A retest, however, on a fresh specimen 7 to 10 days later may be desirable, particularly with patients who may be in the early stages of the disease, in remission, or on steroid therapy.

EXAMPLE 4

Clinical and Laboratory Evaluation of Fluorescent Antinuclear Factor Reagent in Diagnosis of Systemic Lupus Erythematosus The fluorescent antinuclear factor reagent of the present invention has undergone clinical and laboratory evaluation.

Patients

This evaluation was conducted on the sera of 145 subjects incuding 22 with clinically active systemic lupus erythematosus, 21 with clinically inactive systemic lupus erythematosus, 6 with connective tissue disease, and 96 controls (including normals, hospital controls, and other disease states as given in Table II).

Laboratory Tests

Comparisons were made on these 145 subjects with the following preparations: (1) LE cell preparation standard test[2]. (Test A); (2) a desoxyribonucleoprotein (DNP)-latex reagent test[3] (Test B); (3) the fluorescent antinuclear factor test of the present invention (100 subjects); and (4) another fluorescent antinulcear factor test[4] (Test C).

[2] An in vitro serologic test performed on patients' clotted blood for the diagnosis of lupus erythematosus characterized by formation of an "L.E. (lupus erythematosus) cell". Lee., S.L., Clinical Experiences with the LE Cell Phenomenon, J. Mt. Sinai Hosp., 22:74–78 (1955).
[3] Briefly, a test using DMP-latex particles of about 0.81µ wherein the DNP is obtained from fetal thymi and based upon the agglutination principle. Available as the Systemic Lupus Erythematosus (SLE) Latex Test-Kit, Lederle Diagnostics, American Cyanamid Co.
[4] A test similar to that of the present invention, but using calf thymi, not fetal calf thymi, reconstituted from frozen thymi and a touch imprint technique. This technique utilises frozen calf thymus. Fresh slides must be prepared for each test day by thawing a portion of the thymus, touching it to the slide (touch imprint) and then "fixing" slide with acetone. Slides are then used on fluorescent ANF test.

The results are presented in Tables I and II. In addition, titration data for the fluorescent antinuclear factor test of the present invention and the DNP-latex reagent test (Test B) are given in Table III.

Laboratory Results

Excellent agreement was obtained throughout between the DNP-latex reagent test (Test B) and Test A: 82% vs. 86% positive for clinically active cases, 19% vs. 19% positive for clinically inactive cases, 100% vs. 83% negative for connective tissue disease cases (reflecting somewhat greater specificity for the DNP-latex reagent test) and 99% vs. 99% negative for control subjects. The more sensitive Test C and the fluorescent antinuclear factor test of the invention showed greater specificity for the preparation of the present invention than for Test C preparation: 89% vs. 82% positive for clinically active cases, 58% vs. 71% positive for clinically inactive cases, 67% vs. 50% negative for connective tissue disease cases, and 100% vs. 94% negative for control subjects. Both Test C and that of the present invention showed greater reactivity and less specificity than the DNP-latex reagent (Test B) and Test A.

TABLE I

Summary of the Evaluation of the Fluorescent Antinuclear Factor Tests and the DNP-Latex Test in the Laboratory Diagnosis of Systemic Lupus Erythematosus

| Disease State | Positive Reactors | | | | | | | |
|---|---|---|---|---|---|---|---|---|
| | LE Cell Prep Test A | | Test B | | Test C | | Fluorescent Antinuclear Factor Test of Invention | |
| Clinically Active Lupus | 19/22 | (86%) | 18/22 | (82%) | 18/22 | (82%) | 17/19 | (89%) |
| Clinically Inactive Lupus | 4/21 | (19%) | 4/21 | (19%) | 15/21 | (71%) | 11/19 | (58%) |
| Connective Tissue Disease | 1/6 | (17%) | 0/6 | (0%) | 3/6 | (50%) | 2/6 | (33%) |
| Controls+ | 1*/96 | (1%) | 1*/96 | (1%) | 6/96 | (6%) | 0/56 | (0%) |
| Totals | 25/145 | (17%) | 23/145 | (16%) | 42/145 | (29%) | 30/100 | (30%) |

+Normal and hospital control sera and other disease states as listed in Table II.
*SLE Syndrome procainamide induced.

TABLE II

Evaluation of the Fluorescent Antinuclear Factor Tests and the DNP-Latex Reagent Test in the Laboratory Diagnosis of Systemic Lupus Erythematosus

| Diagnosis | No. of Sera Tested | LE Cell Prep Test | | Fluorescent AN-F Tests | | | | | |
|---|---|---|---|---|---|---|---|---|---|
| | | Test A | | Test C | | Test of the Invention | | Test B | |
| | | Pos. | Neg. | Pos.* | Neg. | Pos.* | Neg. | Pos. | Neg. |
| SLE (Clinically Active) | 22 | | | 18 | 4 | 17/19$^c$ | 2 | 18 | 4 |
| SLE (Clinically Inactive$^a$) | 21 | 4 | 17 | 15 | 6 | 11/19$^d$ | 8 | 4 | 17 |
| Connective Tissue Disease: | | | | | | | | | |
| Polyarthritis | 2 | 1 | 1 | 1 | 1 | 1 | 1 | | 2 |
| Rheumatoid Arthritis | 2 | | 2 | | 2 | | 2 | | 2 |
| Scleroderma | 2 | | 2 | 2 | | 1 | 1 | | 2 |
| Other Disease States: | | | | | | | | | |
| Anemias | 6 | | 6 | | 6 | | 6 | | 6 |
| Candida Septicemia | 1 | | 1 | | 1 | | 1 | | 1 |
| Cardiac Arrhymia$^b$ | 1 | 1 | | 1 | | | 1 | 1 | |
| Cholecystitis | 1 | | 1 | 1 | | | 1 | | 1 |
| Dyscrasia (Plasma Cells) | 1 | | 1 | | 1 | | 1 | | 1 |
| Infectious Mononucleosis | 1 | | 1 | | 1 | | 1 | | 1 |
| Multiple Myeloma | 1 | | 1 | | 1 | | 1 | | 1 |
| Myelofibrosis | 1 | | 1 | | 1 | | 1 | | 1 |
| Rheumatic Heart Disease | 1 | | 1 | | 1 | | 1 | | 1 |
| Thrombophlebitis | 2 | | 2 | | 2 | | 2 | | 2 |
| Normals and Hospital Controls | 80 | | 80 | 4 | 76 | | 40 | | 80 |
| Totals | 145 | 25 | 120 | 42 | 103 | 30 | 70 | 23 | 122 |

*Criteria for a positive fluorescent antinuclear factor test is sera positive at a 1:10 dilution or greater.
$^a$Systemic lupus erythematosus clinically inactive meeting the criteria of Siegel et al. (no fever, active arthritis, or other acute inflammatory manifestations).
$^b$SLE syndrome procainamide induced.
$^c$Three sera not tested.
$^d$Two sera not tested.

TABLE III

Summary of the SLE Serum Antibody Titers Obtained with the Fluorescent Antinuclear Factor Test of the Invention and DNP-Latex Reagent Test

| Diagnosis | No. of Sera Tested | SLE DNP Latex Test Serum Titers | | | | No. of Sera Tested | Fluorescent AN-F Test of Invention Serum Titers | | | |
|---|---|---|---|---|---|---|---|---|---|---|
| | | 1:1–1:10 | 20–80 | 160–320 | 320 | | 1:1–1:10 | 20–80 | 160–320 | 320 |
| SLE Clinically Active | 22 | 3 | 6 | 5 | 4 | 19 | 0 | 3 | 5 | 9 |

TABLE III-continued

Summary of the SLE Serum Antibody Titers Obtained with the Fluorescent Antinuclear Factor Test of the Invention and DNP-Latex Reagent Test

| Diagnosis | No. of Sera Tested | SLE DNP Latex Test Serum Titers | | | | No. of Sera Tested | Fluorescent AN-F Test of Invention Serum Titers | | | |
|---|---|---|---|---|---|---|---|---|---|---|
| | | 1:1–1:10 | 20–80 | 160–320 | 320 | | 1:1–1:10 | 20–80 | 160–320 | 320 |
| SLE Clinically Inactive | 21 | 3 | 0 | 0 | 1 | 19 | 3 | 1 | 5 | 2 |
| Connective Tissue Control | 6 | 0 | 0 | 0 | 0 | 6 | 2 | 0 | 0 | 0 |
| Normal and Hospital Control Sera and Other Disease States Listed in Table II | 96 | *1 | 0 | 0 | 0 | 56 | 0 | 0 | 0 | 0 |

*SLE Syndrome Procainamide induced.

Based upon the above clinical and laboratory evaluation it was concluded that:

1. Twenty-two patients with clinically active systemic lupus erythematosus were positive in 82% to 89% with all tests: 82% with the DNP-latex reagent test (Test B), 89% with the fluorescent antinuclear factor test of the invention, 82% with Test C and 86% with Test A.
2. Twenty-one patients with clinically inactive systemic lupus erythematosus were negative in 81% with both Test A and DNP-latex reagent test (Test B). The test of the present invention and Test C, which are more reactive, gave negative values in 42% and 29%, respectively, for the test of the present invention and Test C preparations; the test of the present invention was therefore, more specific.
3. Six patients with connective tissue disease were negative in 83% and 100%, respectively, with Test A and the DNP-latex reagent test (Test B). The latter test, therefore, showed greater specificity. The more reactive test of the present invention and Test C gave negative values in 67% and 50%, respectively, for the test of the present invention and Test C; the test of the present invention was, therefore, more specific.
4. Ninety-six normal subjects and hospital control patients were negative in 99% for both Test A and the DNP-latex reagent test. The more reactive test of the present invention and Test C gave negative values in 100% and 94%, respectively, for the test of the present invention (56 cases) and Test C (96 cases) preparations; the test of the present invention was, therefore, more specific.

It is contemplated that one use of the diagnostic reagent of the present invention is that of a confirmatory test in the diagnosis of systemic lupus erythematosus.

We claim:

1. A method for preparing a dry diagnostic reagent fixed on a microscope slide for the detection of human antinuclear factor in human serum or plasma in an immunofluorescent test for the diagnosis of systemic lupus erythematosus and other autoimmune diseases which comprises:
   a. sieving only fetal calf thymus to obtain dispersed thymocyte cells therefrom;
   b. suspending said dispersed thymocyte cells in isotonic buffered saline solution to a cell count of about $1.0–1.5 \times 10^6$ cells/ml.;
   c. placing at least one portion of about 0.05 ml. of said dispersed thymocyte cell suspension on a microscopic slide;
   d. drying said amount of said dispersed thymocyte cell suspension on said slide;
   e. fixing said dried cell suspension with modified Carnoy's solution;
   f. washing said fixed suspension with water; and
   g. drying said fixed and washed suspension.

2. The method of claim 1 including the additional step of placing said dried, fixed and washed slide in an air tight container with dessicant.

3. A dry diagnostic reagent fixed on a microscope slide for the detection of human antinuclear factor in human serum or plasma in an immunofluorescent test for the diagnosis of systemic lupus erythematous and other autoimmune diseases comprising the dry diagnostic reagent prepared by the method of claim 1.

4. In a method of detecting human antinuclear factor in a test sample for the diagnosis of systemic lupus erythematosus and other autoimmune diseases, said method comprising an immunofluorescent slide test employing an antigen reagent dried on a slide, the improvement comprising employing as said reagent the dry diagnostic reagent prepared by the method of claim 1.

* * * * *